United States Patent [19]

Christinger

[11] 4,441,951
[45] Apr. 10, 1984

[54] MULTIPLE SAMPLING DEVICE HAVING MOLDED VALVE AND HUB

[75] Inventor: Werner Christinger, Franklin Lakes, N.J.

[73] Assignee: Becton Dickinson and Company, Paramus, N.J.

[21] Appl. No.: 282,998

[22] Filed: Jul. 14, 1981

Related U.S. Application Data

[62] Division of Ser. No. 66,818, Aug. 15, 1979, Pat. No. 4,295,477.

[51] Int. Cl.³ .......................... B29C 19/00; A61B 5/14
[52] U.S. Cl. ..................................... 156/245; 128/764; 128/766; 156/242; 156/293; 156/294
[58] Field of Search ............... 156/245, 242, 293, 294; 128/766, 764, 763, 274, 276, 218 NV

[56] References Cited

U.S. PATENT DOCUMENTS

| | | | |
|---|---|---|---|
| 3,469,572 | 9/1969 | Nehring | 128/766 X |
| 3,817,240 | 6/1974 | Ayres | 128/766 |
| 3,848,579 | 11/1974 | Villa-Real | 128/766 |
| 4,106,497 | 8/1978 | Percarpio | 128/766 |
| 4,134,512 | 1/1979 | Nugent | 128/764 X |
| 4,212,308 | 7/1980 | Percarpio | 128/766 |

FOREIGN PATENT DOCUMENTS 2349996  2/1974  Fed. Rep. of Germany ...... 128/766

*Primary Examiner*—Edward C. Kimlin
*Assistant Examiner*—Timothy W. Heitbrink

[57] ABSTRACT

A multiple blood sampling device is disclosed together with its method of manufacture. The device includes a housing having a chamber therein, a first cannula attached to one end of the housing, a second cannula attached to the other end of the housing, and a one-way valve provided within the housing. Part of the housing is molded around a portion of the valve to securely hold it in place. Another portion of the valve extends into the chamber where it provides valving action in response to the relative pressures in to two cannulas. When one cannula penetrates the blood vessel of a patient and the other punctures the stopper of an evacuated tube, blood is able to flow through the device and into the tube. Backflow is prevented by the one-way valve.

2 Claims, 5 Drawing Figures

MULTIPLE SAMPLING DEVICE HAVING MOLDED VALVE AND HUB

This is a division, of application Ser. No. 066,818, filed Aug. 15, 1979, now U.S. Pat. No. 4,295,477.

BACKGROUND OF THE INVENTION

The field of the invention relates to multiple sampling devices for obtaining blood samples from a patient, and methods for their manufacture.

Multiple sampling devices have been used to advantage where one wishes to take a plurality of blood samples from a patient without risk of either backflow or spillage. Such devices often include a plastic needle hub having a chamber therein, an intravenous cannula attached to one end of the hub, a second cannula attached to the other end of the hub, and a one-way elastomeric valve positioned within the chamber. Two particularly advantageous assemblies are described in commonly assigned Ser. Nos. 915,670 and 915,671, both filed June 15, 1978. U.S. Pat. Nos. 3,817,240 and 3,874,367 are further examples of needle assemblies which are now known to the art.

According to present techniques for manufactuing needle assemblies, first and second polymeric hub assemblies are molded. An elastomeric valve is positioned upon receiving means on one hub, and the two hubs may thereafter be joined by conventional methods. Cannulas may be secured to the respective hub assemblies so that a fluid may flow from one cannula, through the valve within the hub assembly, and out through the other cannula. Epoxy may be used for attaching the cannulas to the hub assemblies either before or after they are joined.

SUMMARY OF THE INVENTION

In order to provide an inexpensive and extremely reliable multiple sampling apparatus, the valve and hub are molded in a two-material molding machine such that at least a portion of the valve is encased by a hub portion. The position of the valve is accordingly fixed with respect to the hub so that malfunction due to dislodgement is practically impossible. After pre-assembly of the cannulas into respective first and second hub assemblies, the two halves are joined together permanently.

According to one embodiment of the invention, a sleeve valve is utilized for preventing backflow to the patient through the intravenous cannula. The valve has a bore therein for accomodating the distal end of the intravenous cannula. It also includes an enlarged portion surrounded by the hub which effectively holds it in place. The cannula is slotted near its distal end and the slot is covered by the sleeve portion of the valve. When suction is applied through the use of an evacuated tube, the valve opens to allow blood to pass through the slot and into the tube. Should back pressure occur, the valve will close tighter.

DETAILED DESCRIPTION OF THE INVENTION

FIGS. 1-4 illustrate, in sequence, a series of steps for producing the multiple sampling device which is the subject of the invention.

Figure 1:
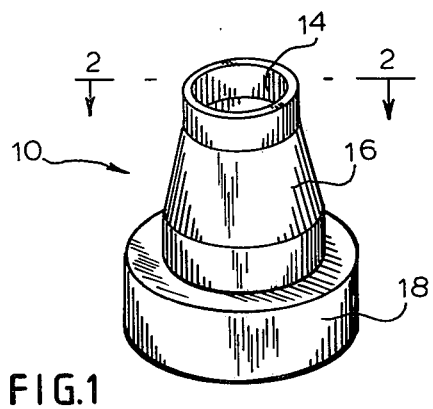
FIG. 1 is an isometric view of a sleeve valve molded to a desired shape.
Figure 2:
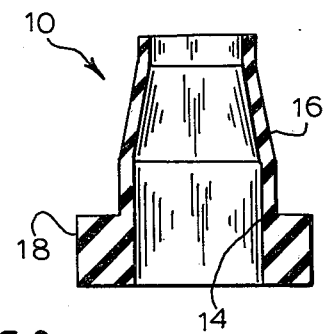
FIG. 2 is a section elevation view of the sleeve valve of FIG. 1.
Figure 3:
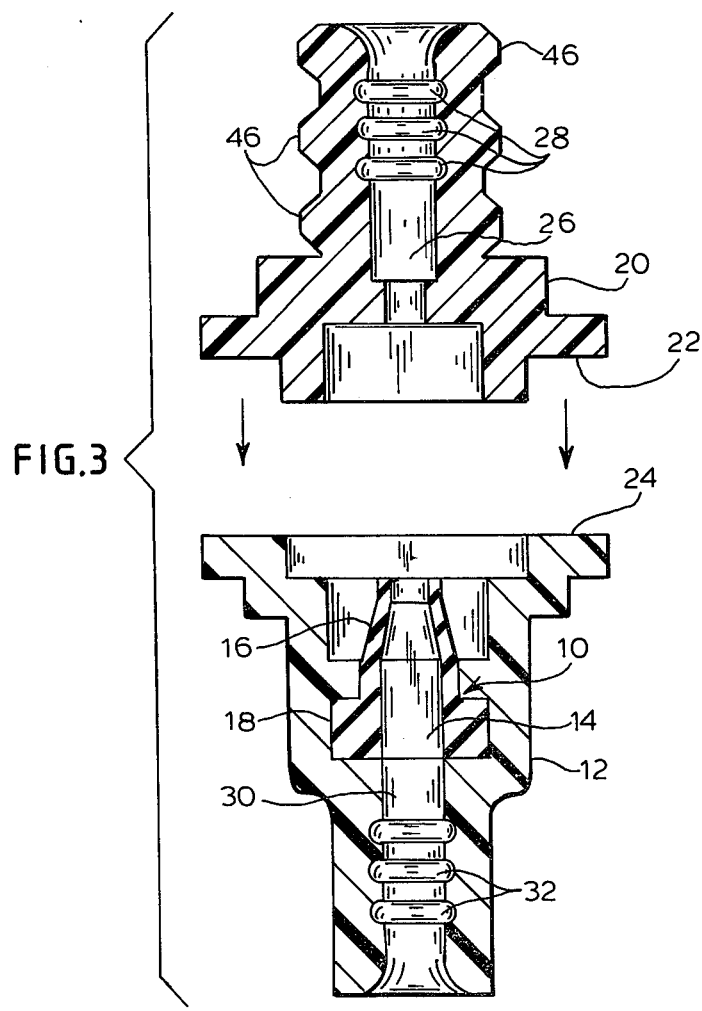
FIG. 3 is a sectional elevation view of a needle hub assembly having a valve molded therein as it is assembled to a second hub assembly.

A two material molding machine is used for molding the valve 10 and "intravenous" plastic hub 12. The valve is molded first to produce a structure as shown in FIG. 1. A thermoplastic elastomer is utilized for the valve material. The valve shown in the drawings is intended to function as a sleeve valve in a manner to be explained later. It has a generally tubular configuration with a bore 14 passing axially therethrough. One end portion thereof includes flexible conical walls 16. The other end includes an axially extending rim 18 giving the valve a hit-shaped appearance.

Once the valve is molded within an appropriately shaped cavity in the molding machine, the core with the valve on it is indexed into a second cavity. (The core is the part of the mold about which the valve is formed, and creates the bore 14 therein). The second cavity is constructed so as to give the intravenous hub 12 its desired shape. This hub is molded around the rim 18 and a portion of the conical walls. A one-piece structure is created with the encased rim preventing any possible displacement of the valve.

A second hub 20 is molded in a conventional manner. It has a surface 22 adapted to mate with the distal surface 24 of the intravenous hub. A bore 26 is provided for accomodation of a cannula. Several circumferential grooves 28 are formed in the walls defining the bore. The intravenous hub 12 is similarly formed with a bore 30 and circumferential grooves 32.

An intravenous cannula 34 is inserted within bore 30. Epoxy may be utilized within the grooves 32 to secure the cannula. Additional epoxy 36 is employed near the opening of the bore 30. A second cannula 38 having an end adapted for puncturing the stopper of an evacuated collection tube is secured within bore 26. The method of attachment is similar to that of the intravenous cannula 34.

Figure 4:
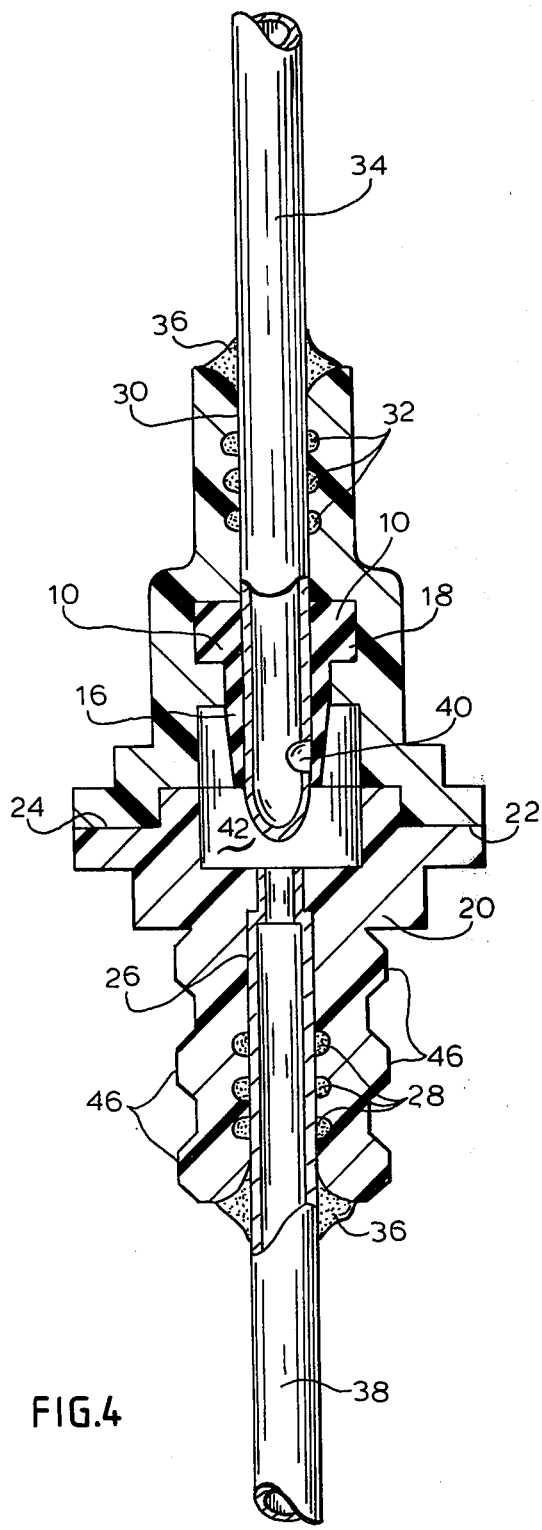
FIG. 4 is a sectional elevation view of a blood sampling apparatus after assembly of the valve, hubs, and a pair of cannulas.

The cannulas are then covered by shields (not shown), and the two hubs are permanently joined along their mating surfaces. The assembly shown in FIG. 4 is thereby created. Valve 10 occludes a slotted opening 40 in the intravenous cannula 34. A chamber 42 is created into which the slotted portion of the cannula extends. The flexible conical walls 16 also extend into the chamber so that they are free to move in and out of contact with the cannula so as to open or close the slot.

Figure 5:
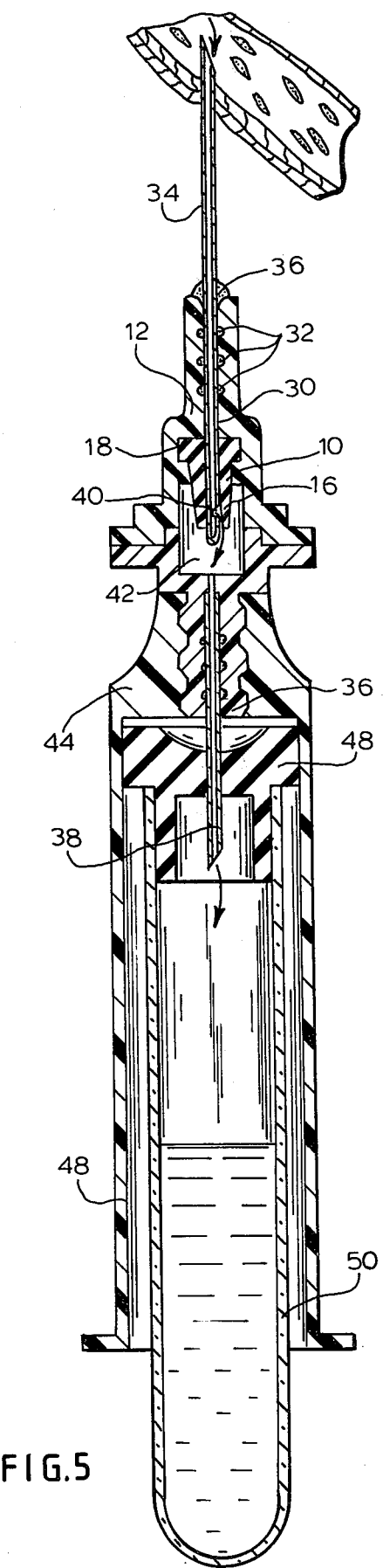
FIG. 5 is a sectional elevation of the blood sampling apparatus in use.

To use the device a holder 44 for evacuated tubes is attached to a threaded portion 46 of the hub 20. The pointed tip of the intravenous cannula penetrates a vessel (such as a vein). The stopper 48 of an evacuated tube 50 is pierced by the tip of cannula 38. This creates a partial vacuum in the chamber 42. Due to the vacuum, the flexible walls 16 open a sufficient amount to allow blood to pass through the slot 40, into the chamber 42, and through the cannula 38 into the tube 50. FIG. 5 is illustrative of this action.

When the tube is filled and the vacuum dissipated, the resilience of the valve walls 16 causes them to reassume their normal position occluding the slot. Since the end of the hollow cannula 30 is closed, there will be no fluid communication between the cannula and the chamber. Should back pressure occur, the valve will close tighter. The device permits multiple sampling as the same venipuncture may be used to fill a number of collection tubes without spillage. The valve prevents any flow of blood while the tubes are exchanged.

What is claimed is:

1. A method for manufacturing a multipled blood sampling device adapted to be coupled with an evacuated container to obtain blood samples from a patient, comprising the steps of:

molding a one-way valve into a desired form including a first portion and a second portion;

molding a first housing part around the first portion of said valve so as to securely attach it thereto, molding a second housing part having a chamber around said second portion of said one-way valve so that said second portion freely extends into said chamber;

attaching a first cannula to said first housing part;

attaching a second cannula to said second housing part, joining said first and second housing parts together permanently, and the valve, housing parts, and cannulas being assembled in such a manner that blood is able to flow through the first cannula, the one-way valve and chamber in said housing parts, and into the second cannula when suction is applied at said second cannula, the valve arranged to prevent any backflow from said second cannula to said first cannula.

2. A method as described in claim 1 wherein the second portion of said valve is molded in the form of a sleeve which can fit over an end of a cannula, the first portion of the valve is molded to include a peripherally extending rim, and said first housing part is molded around said rim.

* * * * *